United States Patent [19]

Sakai et al.

[11] Patent Number: 5,031,112
[45] Date of Patent: Jul. 9, 1991

[54] SYSTEM FOR DETECTING DEFECTIVE PORTIONS IN DATA RECORDING PORTIONS OF OPTICAL RECORDING MEDIUM

[75] Inventors: Yorihiko Sakai, Tokyo; Yasushi Ota, Sendai, both of Japan

[73] Assignee: Dai Nippon Insatsu Kabushiki Kaisha, Tokyo, Japan

[21] Appl. No.: 363,600

[22] Filed: Jun. 7, 1989

[30] Foreign Application Priority Data

Jun. 8, 1988 [JP] Japan ................. 63-141411

[51] Int. Cl.⁵ .............. G01N 21/32; G06F 15/20
[52] U.S. Cl. ..................... 364/507; 364/552; 356/237; 250/562; 250/563
[58] Field of Search ........... 364/507, 552; 250/559, 250/562, 563, 571, 572; 356/237, 239

[56] References Cited

U.S. PATENT DOCUMENTS

| | | | |
|---|---|---|---|
| 4,292,672 | 9/1981 | Southgate | 364/507 |
| 4,505,585 | 3/1985 | Yoshikawa et al. | 364/507 |
| 4,652,125 | 3/1987 | Bowen et al. | 250/562 |
| 4,665,317 | 3/1987 | Ferriere et al. | 250/562 |
| 4,665,496 | 5/1987 | Ott | 364/552 |
| 4,707,613 | 11/1987 | Nagata et al. | 250/572 |
| 4,900,153 | 2/1990 | Weber et al. | 250/562 |

*Primary Examiner*—Parshotam S. Lall
*Assistant Examiner*—Brian M. Mattson
*Attorney, Agent, or Firm*—Parkhurst, Wendel & Rossi

[57] ABSTRACT

A defect detection system detects defective portions such as scratches, pinholes and dust on a pattern formed surface of a medium such as an optical card, optical disk, holographic memory medium or photomask, on which fine patterns are formed. A light source irradiates a controlled ray to a recording portion as an object of detection of the medium, a position regulating mechanisn contrasts a light receiving position of the recording portion, a reflected ray detector distinctively detects reflected rays from defective portions and normal portions of the medium and a reflected ray controller contacts the reflected rays in a manner that the detector can detect optical data by imaging only the reflected ray from a defective portion without the reflected ray from a normal portion.

16 Claims, 7 Drawing Sheets

SYSTEM FOR DETECTING DEFECTIVE PORTIONS IN DATA RECORDING PORTIONS OF OPTICAL RECORDING MEDIUM

BACKGROUND OF THE INVENTION

The present invention relates to a system for detecting defective portion, such as pinholes, black spots, scratches, dust and the like, occurring in data recording portions of an optical recording medium, such as an optical card, optical disk, holographic memory medium or the like. This invention particularly relates to a defective portion detection system capable of detecting defective portions occurring on the substantial surface of the data recording portion during the production process of the medium, and the system does not read the fine pattern for recording data which is formed in the data recording portion. Furthermore, the system of this invention is applicable to the detection of defective portions of industrial products without an optical recording medium if the products have fine patterns and also in the case where the defective portions are overlapped on the fine patterns. The industrial products, for example, are photomasks used in the production of semiconductor devices.

An optical card is an example of the optical recording medium and is generally formed in the size of 85.5 millimeters (mm) long, 54.0 mm wide side and 0.8 mm thick, and this size of card conforms to the standard of International Organization for Standardization (IOS). The data recording portion of the optical card is capable of recording a maximum of 2 mega-bytes of data, and it is possible to extremely increase recording capacity in the same area compared with a magnetic card capable of recording a maximum of 72 bytes of data.

FIGS. 1 to 3 generally show an optical card 1. In FIG. 1, a data recording portion 2 is formed within the specific extent on the card 1. The data recording portion 2, as shown in FIG. 3 in enlarged detail, comprises a recording track 2a being about 7 microns ($\mu$m) in width and having pits 3, and a tracking groove 2b being about 3 $\mu$m in width and having pitches of 10 $\mu$m. The card 1 comprises, as shown in FIG. 2, a substrate 4 having the same shape as the card 1, a first metal layer 5 having the same extent of the portion 2 on a side of the substrate 4 and stable characteristics against laser rays, a second metal layer 6 stacked on the first layer 5 and melted by the laser rays so as to react with a third metal layer mentioned after the third metal layer 7 stacked on the second layer 6 and being a metal-oxide thin layer either coloring or discoloring on the basis of the reaction with the second layer 6 by the laser rays, and a protective layer 8 having the same shape as the substrate 4 and covering the data recording portion 2.

The optical card 1 will happen to have defective portions 9, such as pinholes, black spots, scratches, dust or the like, as shown within a circle C of FIGS. 1 and 3 and in FIG. 2, until the card 1 is completed as a product through some stack steps. The defective portions 9, as shown in FIG. 3, occur on both the recording track 2a as a portion 9a and on the tracking groove 2b as a portion 9b. The defective portion 9b on the groove 2b does not function as a fatal defect to the card 1, but in case the defective portion 9a occupies the greater part of the track 2a over 20 $\mu$m in diameter, the card 1 will have a fatal defect as an optical card. The track 2a has the pits 3 for recording data, which are formed by melting the second metal layer 6 by radiation of a predetermined quantity of laser rays. There are three types of optical cards which are a retrievable type, an add-on type, and a rewritable type. The retrievable type card has specific data stored in the recording portion and is only read by readers. The add-on type card is offered to users in a state without any data recorded thereon and is capable of recording the desired data one at a time. For both types, the optical card 1 can have the recorded data read in the manner that the pits 3 have applied laser rays having the quantity less than one used at recording and the reader (not shown) reads out the presence or absence of the pits 3. If defective portions 9 exist on the protection layer 8 or the like, the portions 9 are written or read as incorrect data by laser rays upon writing or reading.

Accordingly, in order to prevent the circulation of the optical recording medium such as optical cards having fatal defects, it is necessary to detect any fatal defects before shipping.

There are two conventional methods for detecting fatal defects existing on the data recording portion 2.

One method is to detect the defective portions 9 on the recording portion 2 by the human sense of sight by using optical means, such as a microscope. This method is a sensory test to which the skilled inspector having a superior ability of inspection is required.

The other method is to detect the defective portions 9 on the recording portion 2 by other than human means, by processing the pattern or signal conversion of the image which is imaged by an image pick up means. This method is based on the principle that the portion 2 of the card 1 as an object of detection is once converted into image data. The detection for defective portions by processing the signal conversion is to output defective detection signals showing the occurrence of the defective portions 9 in the manner that respective portions 2 of two optical cards 1 are imaged and converted into signals, respectively, and both the signals are compared each other so as to detect the defect by the difference in both signals. The detection by pattern processing uses a so-called pattern matching method wherein the imaged pattern of the portion 2 as an object of detection is compared with a standard pattern. If both the patterns have different parts, the defect detection signal is output by regarding it as a defective portion 9.

However, both conventional systems for detecting the defective portions have the following problems.

At first, the defect detection system by the human sense of sight by using the microscope has the problem that the inspection work is complicated because the inspector must work with his hands to detect the defect of cards, and it is necessary to have many inspectors. As the method using this system is a sensory test, the inspector is easily influenced by his fatigue or the like, thereby there is the problem of deteriorating accuracy and reliability of inspection.

Secondly, the first defect detection system using images has a problem in that because an object of comparison is necessary in order to compare both signals, the entire constitution of the system is large-scale and complicated.

Furthermore, the second system using images according to the pattern matching method has a problem that the operation of the system is troublesome because standard patterns are interchanged on all such occasions when the shape or extent of the recording portion as object of detection is changed. As the pattern comparing method requires an actual construction having high accuracy, the manufacturing costs of the entire system increase.

SUMMARY OF THE INVENTION

An object of the present invention is to provide a defect detection system capable of immediately detecting only fatal defects broader than a predetermined extent and existing in the industrial products having fine patterns such as a data recording portion of an optical recording medium by means of a detector of an optical system having a simple constitution.

To achieve the above object, a defect detection system according to the present invention comprises an irradiation means for control rays for irradiating a specified light controlled, such as point source rays against an object of the defect detection such as a data recording portion, detection means for reflected rays capable of detecting reflected rays from an optical recording portion as the object, and reflected rays control means provided at the position where the reflected rays from the object can be imaged to the detection means and for controlling the reflected rays in the manner that the detection means detect reflected rays from the defective portions and luminous intensity different from those from normal positions. The present invention can be utilized by the concrete construction that the detection means are comprised of an image pick-up device such as an image pick-up tube, camera tube, solid state image pick-up device, linear sensor (line scanner) or the like, and the control are comprised of an imaging lens which images only the defective portions and does not image the normal positions, such as the tracking groove. For example, a transmission type diffraction grating lens is applicable to the imaging lens.

The irradiation means of control rays is comprised of, for example, a point source in order to contrast the defective portions with the normal portions and to emphasize the contrast between these portions. If light having the predetermined width or stretch is used as the control rays, the contrast between the defective portions and the normal portions is deteriorated because the reflected rays are irregularly reflected by the normal portions and the defective portions.

As the defect detection system according to the present invention has the above-mentioned configuration, the reflected rays detection means can only detect optical data from the defective portions if the imagery lens as the reflected rays control means is set to have magnifying power capable of only imaging the defective portions and incapable of imaging the normal portions of the optical data recording portion. In the case that the detection means are comprised of the image pick-up device, the device can detect the defective portions by displaying only defects existing within an extent of the data recording portion of an optical card as the object of detection. The image pick-up device can display not only the positions but also the characters of the defective portions. Namely, in a screen of the device, normal portions are displayed as black spot information on the gray screen in accordance with the conditions of the reflected rays, and dust on the recording portion are displayed as white spot information on the gray screen.

To display the above-mentioned information, the image pick-up device as the reflected ray detection means converts optical data from the normal portions within the reflected rays from the object into the predetermined signal to cause the screen to be gray and converts optical data from the defective portions into the different signals having the different amplitude.

As the system to the present invention comprises the irradiation means of the controlled rays such as the point source rays to the object, the reflected ray control means for controlling the reflected rays from the object, and the reflected ray detection means for detecting the rays in the condition that the rays from the defective portions are different from the rays from the normal portions, it is possible to inspect the defective portions of industrial products having fine patterns, such as an optical recording medium having a data recording portion by simple construction and with low manufacturing costs.

If the reflected ray control means are comprised of an imagery lens of which resolving or magnifying power is set in the predetermined value, it has the flexibility to detect defective portions in accordance with size, positions and character to be detected.

Furthermore, it is possible to improve the accuracy and reliability of the inspection in accordance with the present invention because it requires no skill to inspect the defect of cards and the inspector is not tired by defect detection.

DETAILED DESCRIPTION OF THE PREFERRED EMBODIMENTS

There will be described in detail the preferred embodiments of a system for detecting defective portions in a data recording portion of an optical recording medium according to the present invention with reference to the accompanying drawings.

Figure 4:
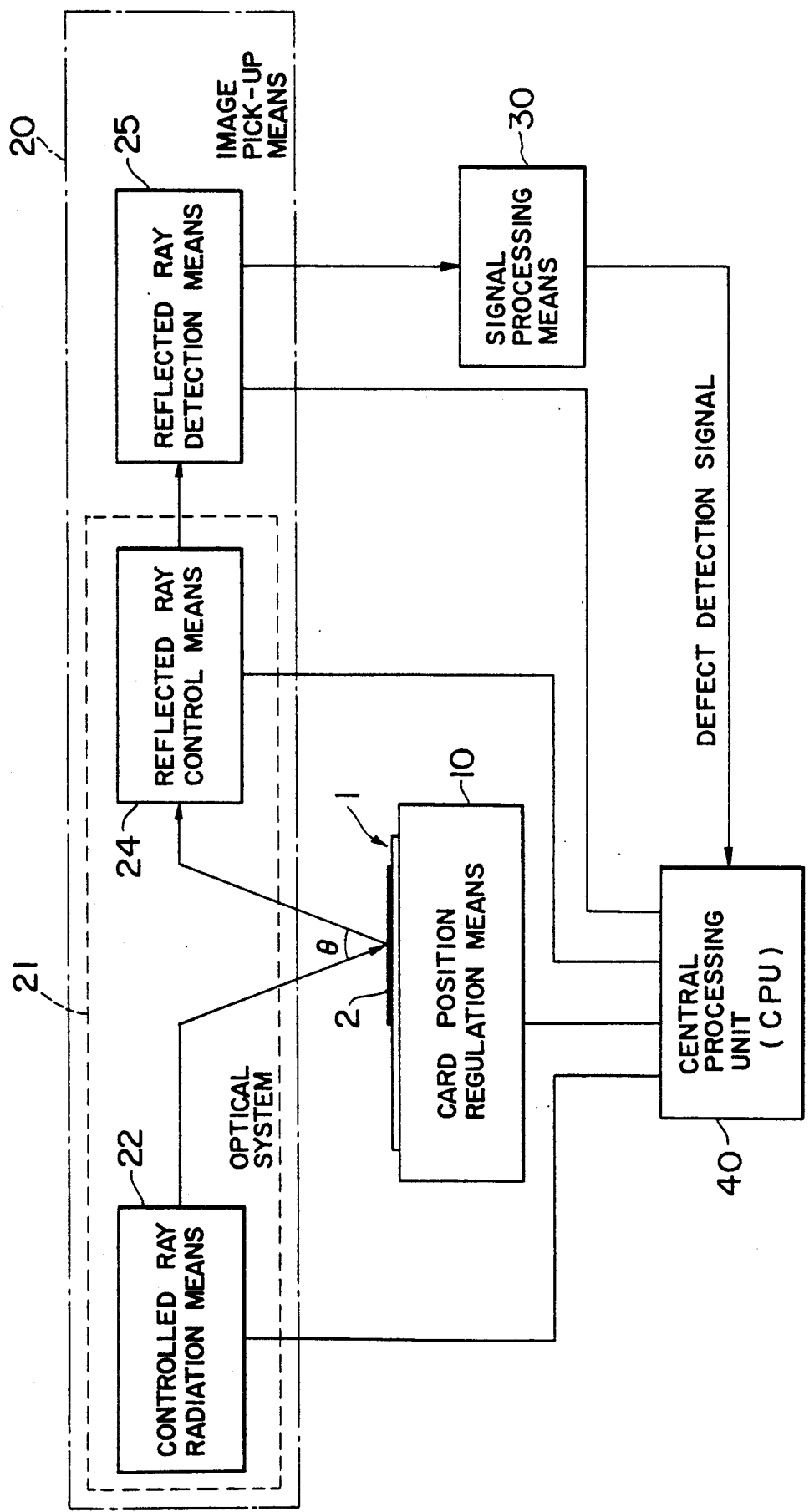
FIG. 4 is a block construction diagram showing the fundamental concept of the defect detection system for the optical recording medium in accordance with the present invention.

At first, the fundamental concept of this invention is explained in accordance with FIG. 4.

The defect detection system of this invention schematically comprises card position regulation means 10, image pick-up means 20, signal processing means 30, and a central processing unit (CPU) 40. The position regulation means is provided to be put on an optical recording medium 1; such as an optical card or optical disk described hereinafter having a data recording portion 2 and to regulate the position of the medium 1 so as to be suitably irradiated by controlled rays. The image pick-up means 20 detects defective portions by imaging an extent of the portion 2 on the basis of reflected rays from the portion 2. The signal processing means 30 receive; optical information within the portion 2 imaged by the image pick-up means 20, converts the optical information into a defect detection signal, and outputs the signal. The CPU 40 controls the regulation means 10 and image pick-up means 20 and outputs a control command to various display means (not shown) on the basis of the defect detection signal output from the signal processing means 30.

Figure 1:
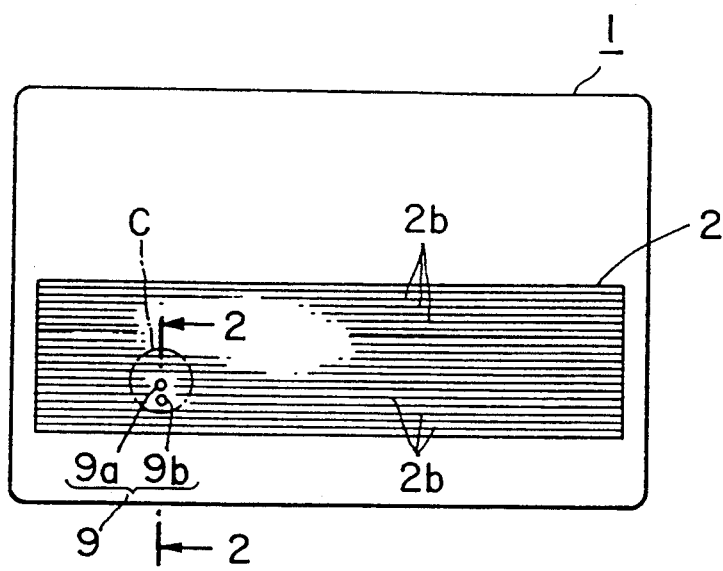
FIG. 1 is a plan view showing a general optical card as an example of an optical recording medium.
Figure 2:
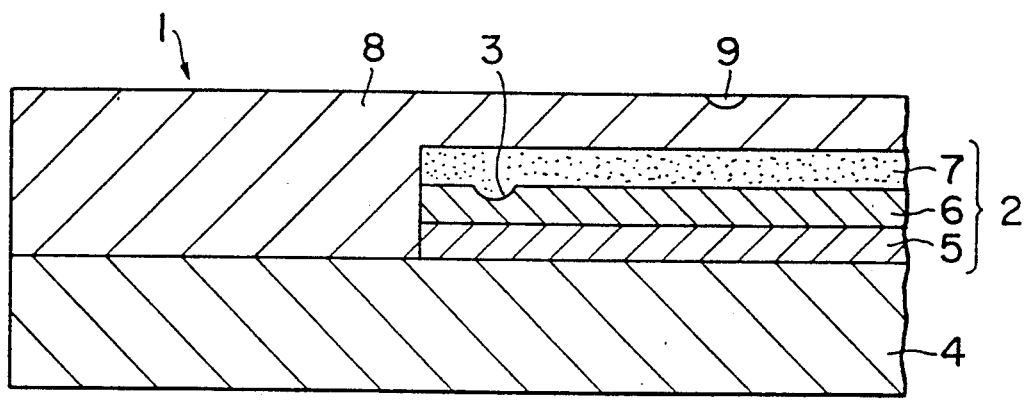
FIG. 2 is an expanded fragmentary sectional view taken on line II—II of FIG. 1 showing the optical card.

The system according to the present invention assumes that controlled rays are regularly reflected at the glossy surface of normal portions in the data recording portion 2, but irregularly reflected at defective portions 9 (shown in FIG. 1). The system of this invention has the feature of providing the image pick-up means 20 by which the regularly reflected rays are not imaged but the irregularly reflected rays from the defective portions are imaged on the basis of the above-mentioned premises. The image pick-up means 20 comprises controlled rays radiation means 22, reflected rays control means 24, and reflected rays detection means 25. The radiation means 22 and control means 24 form in concert an optical system 21 including a condenser lens and an imaging lens. The detection means 25 is capable of the utilization by means of an area sensor (or an image sensor) which planely senses reflected rays within the predetermined two-dimensional extent and converts the rays into signals, a linear sensor (or a line scanner) which linearly senses reflected rays as lines of one dimension and converts the rays into signals.

Next, there will be described the defect detection system according to the first embodiment applying the optical card as the optical recording medium.

Figure 5:
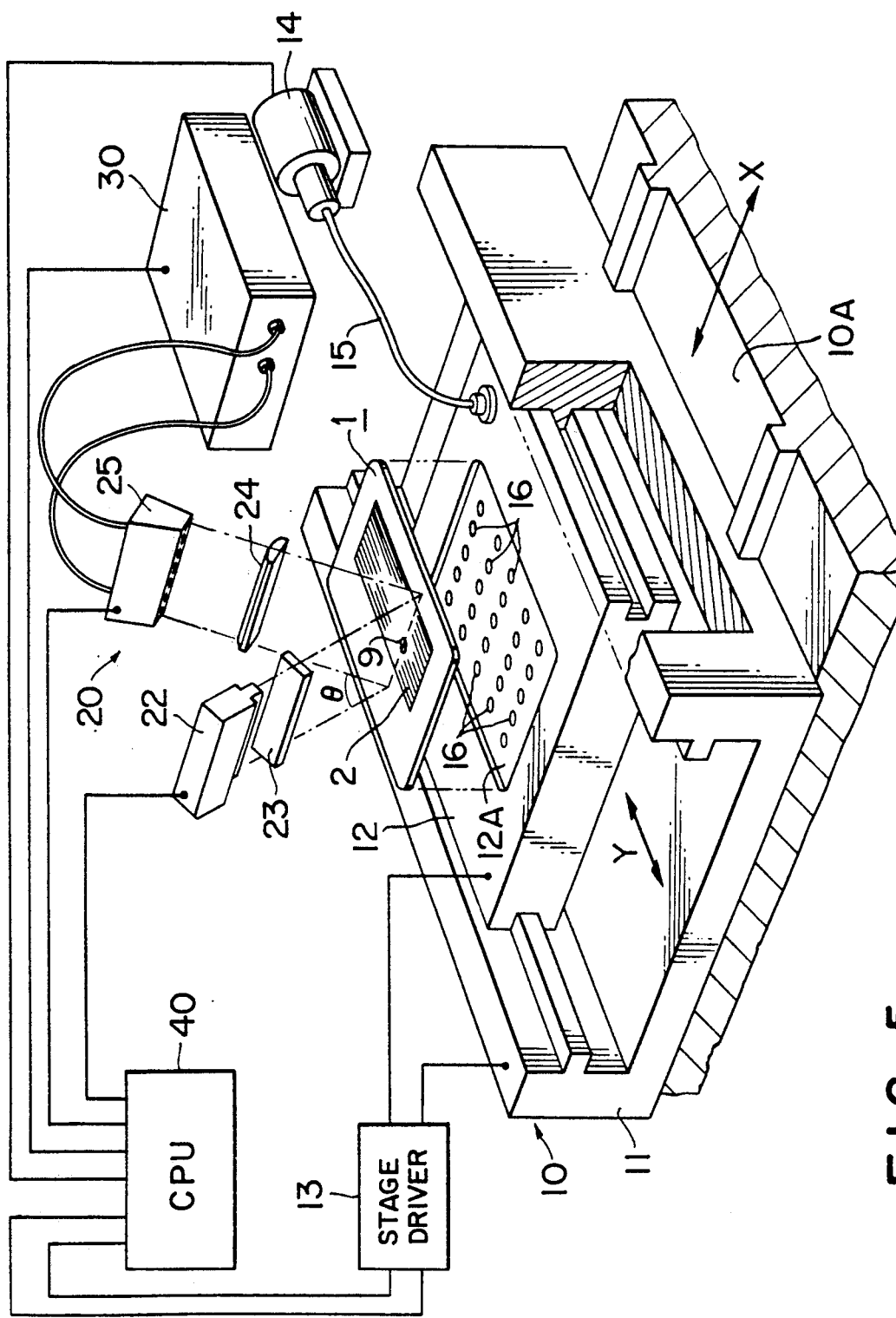
FIG. 5 is a perspective view showing a main arrangement of the concrete system according to the first embodiment of this invention.

As shown in FIG. 5 explaining the fundamental constitution of the first embodiment, an optical card 1 is put on a card position regulating mechanism 10. The regulating mechanism 10 comprises a fundamental stage 10A having an X-direction guide on its upper surface, an X-direction stage 11 movably provided on the fundamental stage 10A capable of sliding in the X-direction shown in FIG. 5, a vacuum suction stage 12 movably provided to the X-direction stage 11 capable of sliding in the Y-direction and holding the optical card 1 by vacuum suction, a stage driver 13 causing the X-direction stage 11 and the vacuum suction stage 12 to move in the X and Y directions, respectively, and a vacuum pump 14 connected to the stage 12 by a tube 15 and absorbing the card 1 by vacuum force through a plurality of suction holes 16 . . . which are open on a card setting surface 12A of the stage 12. The mechanism 10 causes the card 1 to be in the position where the recording portion 2 is within the detectable width of the detection means 25 by the X-directional regulation of the stage 11 and to move in the manner that the stage 12 moves at a speed according to the detecting ability of the means 25 by the Y-directional regulation when the means 25 detects the reflected rays from the portion 2, and this regulation is performed on the basis of command from the CPU 40.

Figure 6:
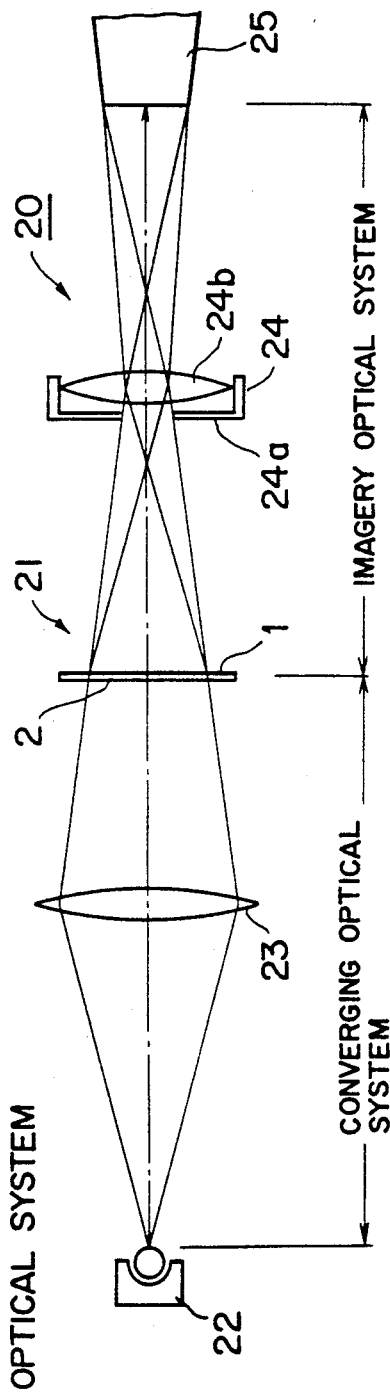
FIG. 6 is an optical path diagram of parallel and reflected rays for explaining the fundamental operation of an optical system in the defect detection system according to this invention.

The image pick-up means 20 comprises, as shown in FIGS. 5 and 6, a light source 22 such as a fluorescent or point source lamp, a condensing lens 23 for condensing the controlled rays from the source 22 within the data recording portion 2, a reflected ray controller 24 for causing the detection means 25 only to image the defective portions 9 and not to image the normal portions of the data recording portion 2, and a linear sensor 25 as the reflected rays detection means applicable to the first embodiment. The reflected rays controller 24 comprises, as shown in FIG. 6, a lengthened diaphragm 24a for regulating the light quantity of the reflected rays from the portion 2, and an imagery lens 24b for imaging the defective portions on the sensor 25 as a white or black image. The optical system 21, as labeled in FIG. 6, is made up of a converging optical system including the source 22 and the lens 23, and an imagery optical system including the controller 24 and the sensor 25. Though FIG. 6 shows the optical path from the source 22 to the sensor 25 as the transmission style because of avoiding the ambiguous arrangement in the figure, the optical path is actually formed in the reflecting optical system having the reflecting surface of the portion 2 of the optical card 1.

Figure 7:
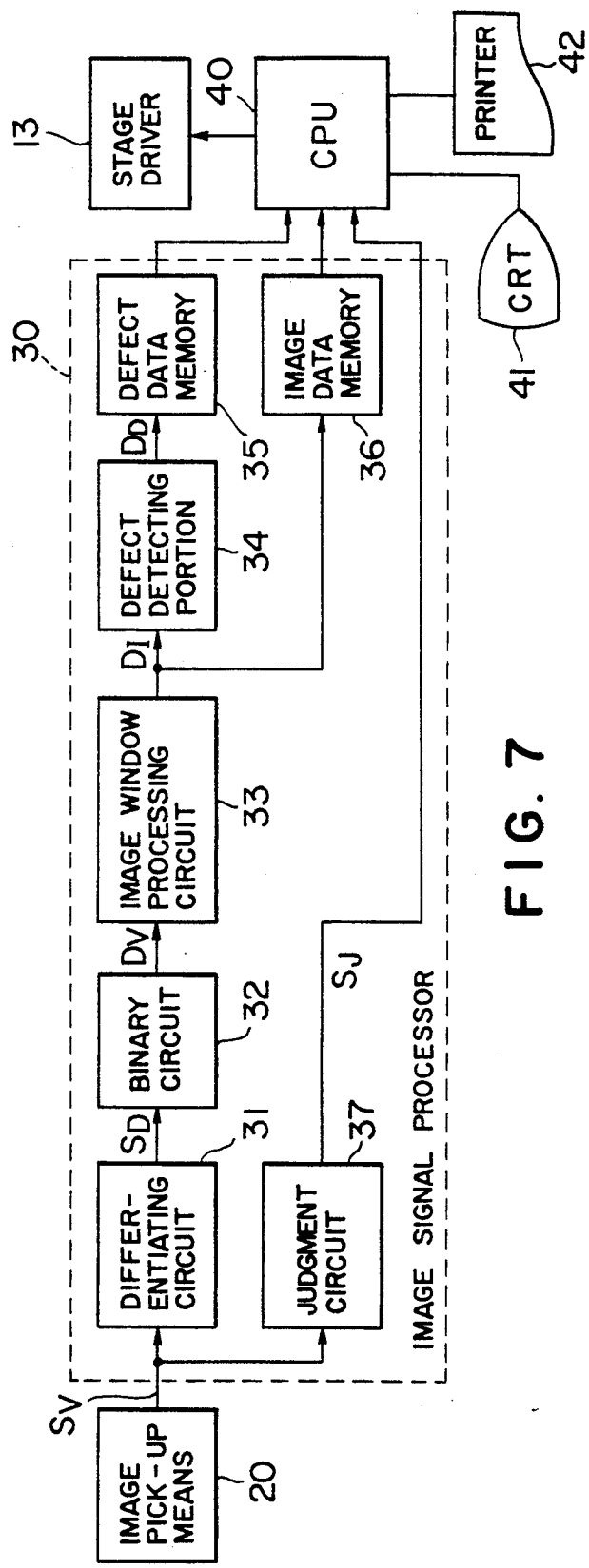
FIG. 7 is a block diagram showing a constitution of a signal processing unit as a signal processing means.

There is shown an image signal processor 30 as one example of the signal processing means in FIG. 7. In FIG. 7 the image signal processor 30 comprises a differentiating circuit 31 for differentiating a video signal $S_V$ (an analog signal) and outputting a differentiated signal $S_D$ to stress portions in the signal $S_V$ corresponding to the defective portions 9, a binary circuit 32 for converting the signal $S_D$ into a binary and digital video data $D_V$ and outputting the data $D_V$, an image window processing circuit 33 for picking up an image data $D_I$ corresponding to an extent for the defect detection in the video data $D_V$ and for ignoring the data value corresponding to an extent without the video data $D_V$, a defect detecting portion 34 for discriminating a kind, position and size of the defective portion including a black defect corresponding to a scratch and a white defect corresponding to the dusts on the basis of the image data $D_I$, a defect data memory 35 for storing various detected data $D_D$ in accordance with the defective portions detected by the defect detecting portion 34, an image data memory 36 for sequentially storing the detected data of every line in order to sequentially transmit the image data $D_I$ to the CPU 40, and a judgment circuit 37 for judging the image valid/invalid to recognize the start and end of defect detection on the basis of the video signal $S_V$ and outputting a judging signal $S_J$ to the CPU 40.

Figure 3:
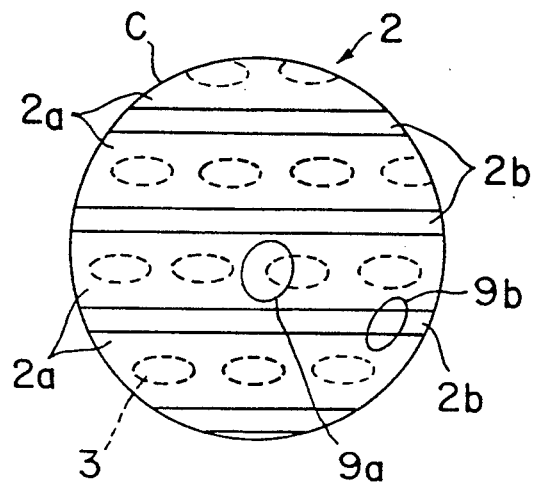
FIG. 3 is an expanded view schematically showing the circle C in the data recording portion of the optical card shown in FIG. 1.

There will be described an optical card, such as the add-on type that cannot be rewritten, showing an example of objects of the defect detection system according to the present invention with reference to FIGS. 1 and 3 showing plane views of the optical card. A recording portion 2 is provided in the center portion of the optical card 1. As partially shown in FIG. 3, a plurality of tracks 2a each having a pitch of 10 μm, are formed in the lateral direction of the recording portion 2 and several thousands lines with an arrangement in rows from top to bottom. Data of the optical card 1 are written to and read out by the reciprocating motion of the regulation mechanism 10, so that so-called guide portions are provided at the starting and finishing ends of each track 2a in order to start and stop with acceleration and deceleration, and inside portions of the guide portions are provided in order to write control data for recording and reproducing. The data recording portion capable of writing data is provided at the inside of these portions and has a plurality of tracks. Each track has strip-shaped and uniform patterns which are called tracking grooves without pits and are several μm (3 μm) in width.

A lot of the data recording portions 2 of the optical cards 1 are within 40 μm in the width short sides. Accordingly, the regulation mechanism 10 and the linear sensor 25 are constructed such that the whole scope of the data recording portion 2 is imaged by main scanning of the linear sensor 25 in the direction of the width of the portion 2 and by sub-scanning of the regulation mechanism 10 in the direction Y.

If the linear sensor 25 has the construction capable of imaging the defective portions over substantially 10 μm on the surface of the optical card 1 on the basis that the tracking groove is several μm in width, only the defective portions over substantially 10 μm are imaged and other portions, such as the tracking grooves, are not imaged at scanning the optical card 1.

Accordingly, the linear sensor 25 of this embodiment uses a one-dimensional charge coupled device (CCD) having four thousand ninety-six (4,096) pixels in order to image a recording portion 2 of 40 mm in width by resolving power of substantially 10 μm. The imaging lens 24 is regulated to have a magnification such that the recording portion 2 being 40 mm in the width is imaged on the imagery surface of the linear sensor 25 having 4,096 pixels. The vacuum suction stage 12 is movably provided to the X-direction stage 11 of the regulating mechanism 10 and fixes the optical card 1 at the predetermined position so as to prevent the image from blurring out of focus of the inspected surface on the basis of the warp of the optical card. As the mechanism 10 comprises the stage 12 having the upper surface of sufficient plane and a level regulator (not shown), the position regulating mechanism 10 of this embodiment has low manufacturing cost in comparison with the specific auto focusing mechanism.

The regulating mechanism 10 causes the optical card to move straight and precisely along the long sides. The accuracy of motion is demanded to be higher than the resolving power of 10 μm at imaging the optical card by the linear sensor. This embodiment uses a mechanism having a positioning accuracy of ±1 μm.

The source 22 illuminates the optical card 1 and uses a fluorescent lamp burning by high-frequency because uniformly illuminating the recording portion along the short ends of the card, namely the long ends of the linear sensor 25. Furthermore, the light source 22 is driven by the power source having the frequency to which the linear sensor 25 can not respond, so as to prevent flickering of the fluorescent lamp. The source 25 can be applied from a point source lamp driven by a direct current power source. THe source 22 applied from the fluorescent or point source lamp has luminous energy regulation and display function in order to maintain appropriate quantity of light.

As shown in FIGS. 5 and 6, an angle $\theta$ is formed by ray axes of the source 22 against the imaging lens 24b and linear sensor 25. THe angle $\theta$ is properly regulated in the manner that the output signal or SN ratio of the linear sensor 25 has suitable value, for example, it is most suitable that the angle $\theta$ is twenty degrees in this embodiment. In the case that the object of detection is transparent, the source 22 is provided in the side opposite to the sensor 25 in the manner that the object is put between the source 22 and the sensor 25.

There will be described the defective portions occurring on the optical card 1. If the card 1 has foreign substances or scratches, these substances and scratches are detected as black defects because the light from the source 22 is absorbed by the substances or scratches so that intensity of reflected rays from the substances or scratches is less than that from other portions. When the optical card 1 has cuts as scratches on its track patterns, reflected rays from the cuts as scratches are stronger than those from normal portions, so that the cuts as scratches are detected as white defects.

How to process signals or data in the defect detection system will be described hereinafter with reference to FIG. 7.

After the video signals $S_V$ are processed by the signal processor 30 in order to abstract defect signals and to recognize positions of the defective portions, the processed signals are output to the CRT 41 and printer 42 through the CPU 40 in order to display and record various defect data, defect patterns, or the like.

There is further described in detail operations of the signal processor 30.

At first, the differentiating circuit 31 processes the video signals $S_V$ (an analogue signal) from the image pick-up means 20 in order to emphasize the defect signals included within the signals $S_V$. The differentiated video signals $S_D$ are digitized in binary value by the binary circuit 32 to convert the signals $S_D$ into digitized video data $D_V$. In this step, the polarity of white defects of the differentiated video signals $S_D$ is opposite to that of the black defects and polarities of the digitized data $D_V$ are opposite to each other in both defects such as rising pulses to falling pulses. This invention can discriminate white defects and black defects on the basis of the above characteristics. A threshold level of the binary circuit 32 is set corresponding to the actual size of the defective portion on the basis of the inspection result obtained by processing hereinunder.

Next, the image window processing circuit 33 picks up the image data $D_I$ corresponding to the extent necessary to the defect detection within the video data $D_V$ corresponding to one line of the linear sensor 25 and compulsorily sets a data value without the image data $D_I$ zero, therefore preventing failure of the inspection by data from unnecessary extent. In the case of the optical card, data of portions without the recording portion as the object of the detection are eliminated as unnecessary image data.

The defect detecting portion 34 recognizes defect (a white defect or black defect), positions and size (or length) of the defects on the basis of the image data $D_I$, synchronized signals (not shown) for the image pick-up means 20, and discriminated result of the white and black defects mentioned above. The defect data $D_D$ corresponding to the king, positions and size of the defects detected by the portion 34, are once stored in the defect data memory 35 and transmitted to the CPU 40 thereafter.

The image data memory 36 is provided for sequential transmission of the image data $D_I$ to the CPU 40. The memory 36 has a pair of memory cells capable of storing the image data $D_I$ of an amount of one line of the linear sensor 25. One cell of the memory 36 receives the image data $D_I$ from the image window processing circuit 33, while the other cell transmits the image data $D_I$ having already received to the CPU 40. The operation of the cells is performed at the same time and alternates each other.

The transmission of the defect data $D_D$ from the memory 35 to the CPU 40 may be performed at the same time as the transmission of the image data $D_I$ from the memory 36 to the CPU 40, but one may be performed before the other if necessary.

The judgment circuit 37 is provided for obtaining the judgment signal $S_J$ to recognize the start and end of detection. The circuit 37 designates the video signal $S_V$ as valid when the signal $S_V$ is more than the predetermined level (signal $S_J$ is ON-state) and invalid without the above state (signal $S_J$ is OFF-state). Accordingly, the judgment signal $S_J$ is set to the ON-state when the optical card 1 is set on the upper surface of the stage 12 and the recording portion 2 is imaged.

Figure 8:
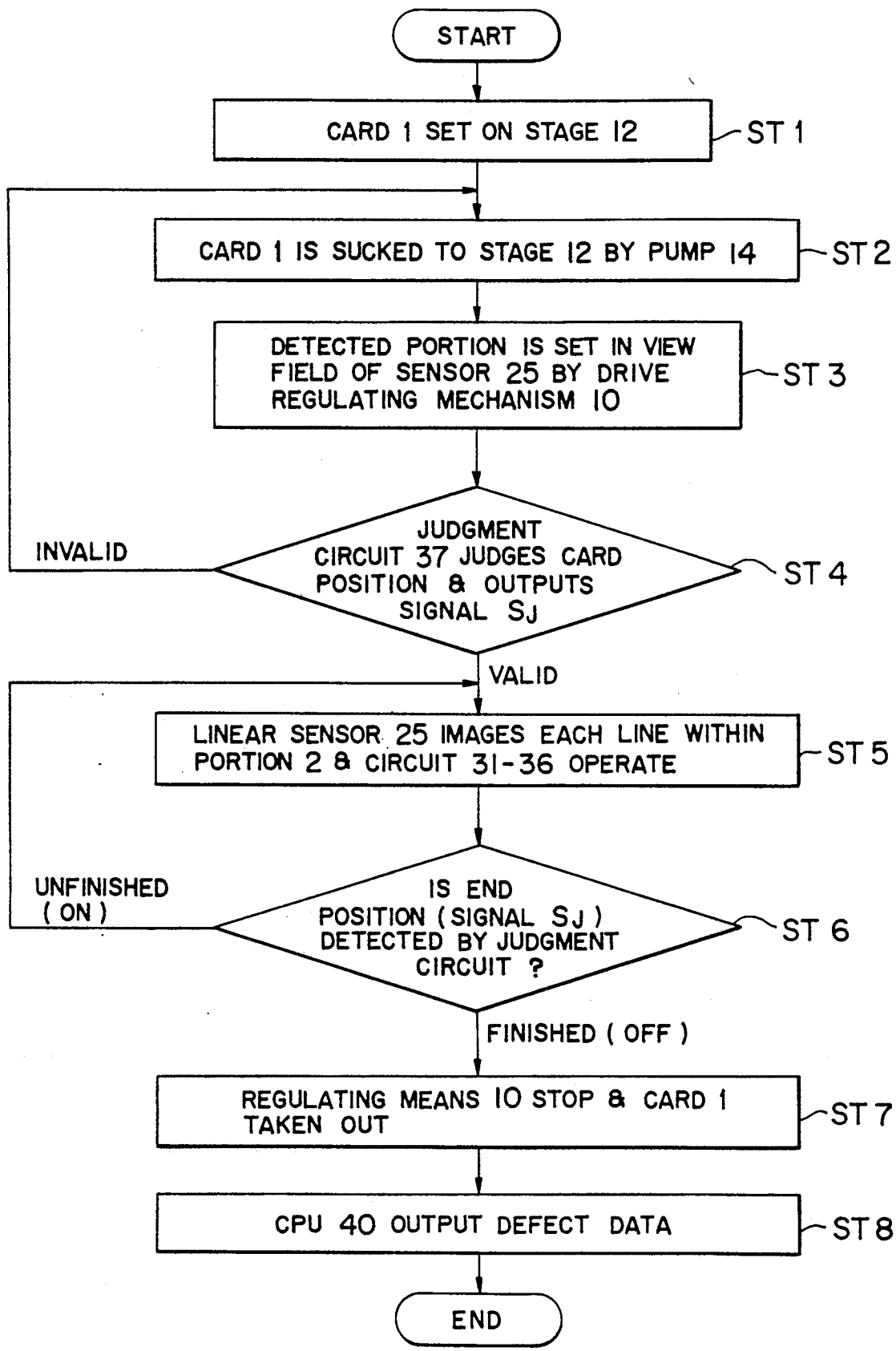
FIG. 8 is a flowchart for explaining an operation of the defect detection system shown in FIG. 5.

With reference to the flowchart shown in FIG. 8, there will be described an example of the operational procedure in the case that the above-mentioned defect detection system performs the defect inspection of the optical card. The signal processor 30 and the CPU 40 are performing the following operational procedure.

(a) The optical card 1 is set on the predetermined position of the vacuum suction stage 12. The optical card 1 positions out of a visual field of the linear sensor 25 (See step ST1 in FIG. 8).

(b) The vacuum pump 14 is driven and causes the stage 12 to suck against the card 1 (See step ST2).

(c) The regulating mechanism 10 starts moving (step ST3).

(d) The judgment signal $S_J$ is ON-state when the regulating mechanism 10 causes the recording portion 2 of the card 1 to be in view field of the linear sensor 25 (step ST4).

(e) The defect data and image data of each line obtained by process of the processor 30 are transmitted to the CPU 40. During this operation, the mechanism 10 continues subscanning at the predetermined speed (step ST5).

(f) Operation described in paragraph (e) continues to the OFF-state of the judgment signal $S_J$ (ST6).

(g) When the judgment signal $S_J$ is the OFF-state, the mechanism 10 stops moving (step ST7).

(h) The stage 12 is cancelled to suck the card 1, and the card 1 is taken out (step ST7).

(i) The CPU 40 outputs the defect data, such as number, size, character and position of the defective portions on the card 1 (step ST8).

In scanning by the position regulating mechanism 10, it is possible to increase the efficiency in operation time by causing the stage 12 to move one line and the linear sensor 25 to scan lines by changing the scanning direction to every other line.

One optical card is inspected within thirty seconds when defect detection is performed under the following operations condition designated in the table.

Main details to inspect a card are as follows:

It takes substantially twenty seconds to scan the optical card, namely to be operated by steps ST3–ST7 (described in paragraphs (c)–(g));

It takes substantially five seconds to set or take out the card (in steps ST1, ST2 and ST7 and paragraphs (a), (b) and (h)); and It takes a few seconds to process data by CPU 40 (in step ST8 and paragraph (i)).

TABLE

| Operational Condition | Result |
| --- | --- |
| Number of pixels of linear sensor 25 | 4,096 pixels |
| Operation clock of linear sensor 25 | 2 MHz (500 nsec/pixel) |
| Resolving power of linear sensor 25 | 10 μm/pixel |
| Magnifying power of imaging lens 24b | One & half times |
| Moving speed of regulating mechanism 10 | 5 mm/sec |
| Transmitting speed from memory to CPU | 500 kByte/sec |

In the case where the object of detection has a large detected area, it is a matter of course to use the regulating mechanism 10 as moving means for moving inspection portions in addition to use as a subscanning means.

Though the optical card 1 is fixed to the vacuum suction stage 12 by sucking air, fixing means are not limited to vacuum adhesion and may be applied by electrostatic adhesion or mechanical cramp.

In the first embodiment using the CCD linear sensor 25 as reflected rays detection means and using the optical card 1 as objects of detection, there is described a detecting operation that the normal portions are not imaged, and the defective portions are only imaged in the recording portion 2.

In this case, the tracking groove 2b is formed in the portion 2, as shown in FIG. 3, having 3 μm in width and 10 μm in pitch, and the sensor 25 has 4,096 cells which are formed 10 μm square (10×10), respectively. The portion 2 as the object of detection is 40 mm in width, while the defective portions 9 to be detected are more than 20 μm in diameter. Under these conditions, the magnifying power of the imagery lens 24b is determined as follows:

$$W_G \leq W_C/n \leq W_D \tag{1}$$

where $W_G$ is the width of the tracking groove, $W_C$ is the width of each cell, n is the magnifying power of the imaging lens, and $W_D$ is the width of the defective portion, on the basis of the above conditions.

$$\left.\begin{array}{l} W_G = 3 \ (\mu m) \\ W_C = 10 \ (\mu m) \\ W_D = 20 \ (\mu m) \end{array}\right\} \tag{2}$$

The magnifying power n is obtained by substituting equations (2) to (2), namely:

$$0.5 \leq n \leq 3.3 \tag{3}$$

As the CCD linear sensor 25 has 4,096 cells, each cell 10 μm in width, the width of a view field $W_V$ and the width of the recording portion 2 are obtained by the following equations (4) and (5) when the magnifying power n is set as 1.0, $$W_V = 4,096 \times 10 = 40,960 \ (\mu m) \tag{4}$$

$$W_R = 40 \times 1000 = 40,000 \ (\mu m) \tag{5}$$

from equations (4) and (5), the linear sensor 25 can be constituted to have the field of view (40,960 μm) capable of imaging the portion 2 (4,000 μm), namely $W_V > W_R$.

As described above, tin the case where the groove 2b having a width of 3 μm and pitch of 10 μm is formed in the portion 2 of 40 mm in width and the defective portions 9 are over 20 μm, the grooves 2b are not imaged, and the portions 9 are only imaged on the linear sensor 25.

The controlled rays irradiation means 22 are applied from the point source ray for the following reason. If the irradiation means 22 uses rays having the predetermined width or extent, the portion 2 is irradiated by rays from many directions on its surface. Accordingly, the reflected rays from the surface of the portion 2 have many directions, so that the defective portions 9 are different from the normal portions in the brightness of the reflected rays. In order to prevent contrast decreasing, this invention uses the controlled rays to limit the angle of incidence of the irradiated light supplied to the portion 2 and to control the direction of the reflected rays, so that it is possible to sharply improve the contrast of the reflected rays between the defective portions and normal portions and to increase the detection accuracy.

There is described hereinunder an optical path of the controlled rays which are irradiated from the light source 22, reflected on the surface of the portion 2 of the card 1, and imaged on the linear sensor 25, according to FIG. 6 showing the optical path in transmission type.

The reflected ray control means 24 has a diaphragm 24a in order to improve the contrast of the reflected rays and the accuracy of the defect detection. That is, in the condition where the diaphragm 24a is stopped down for improvement of the contrast, the light through the diaphragm 24a is transmitted in substantially the center of the imaging lens 24b. It is possible to achieve the improvement of the contrast and resolving power by the uniform reflected rays along the width direction of the portion 2.

Figure 9:
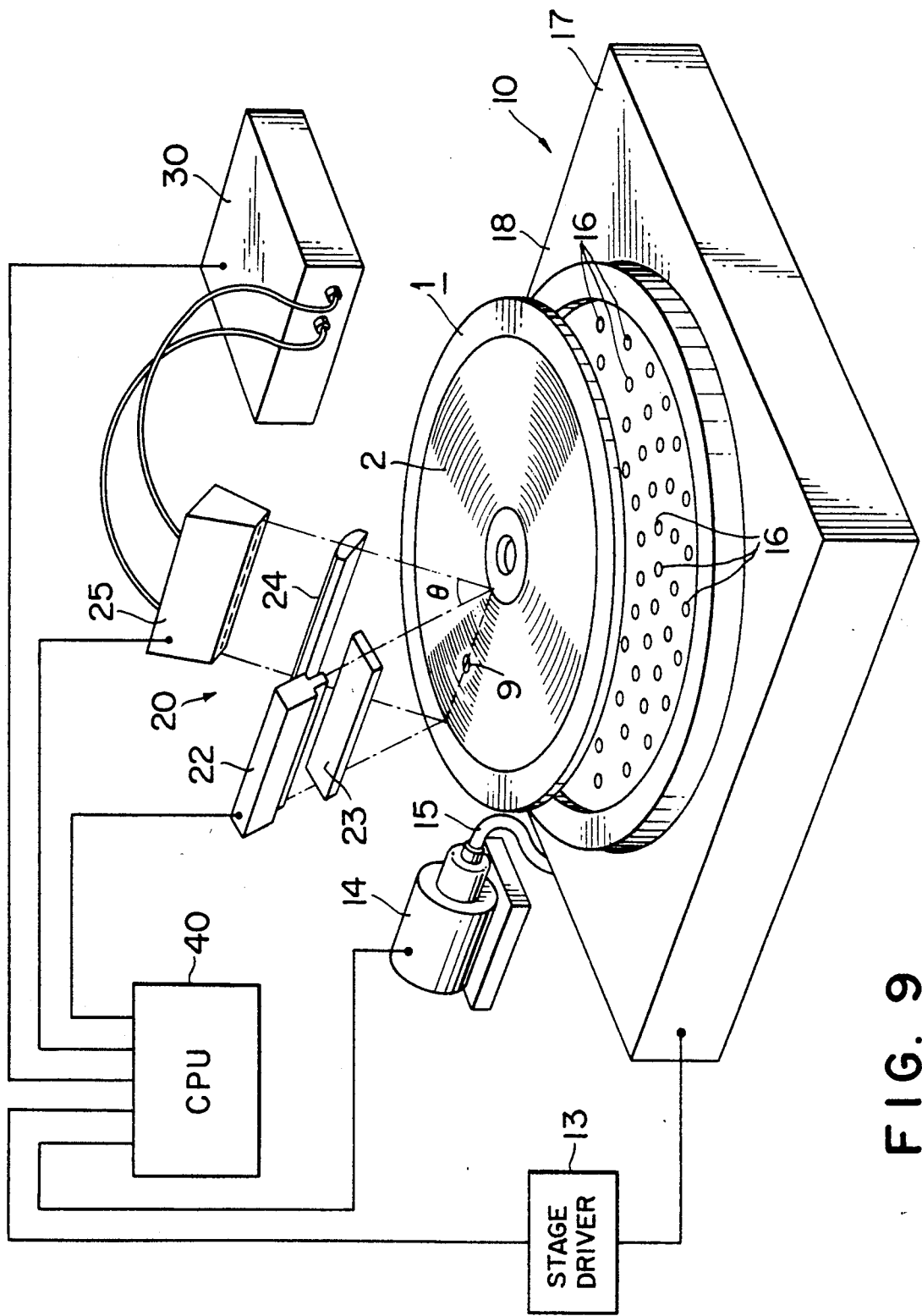
FIG. 9 is a perspective view showing a main arrangement of the concrete system according to the second embodiment of this invention.
Figure 10A:
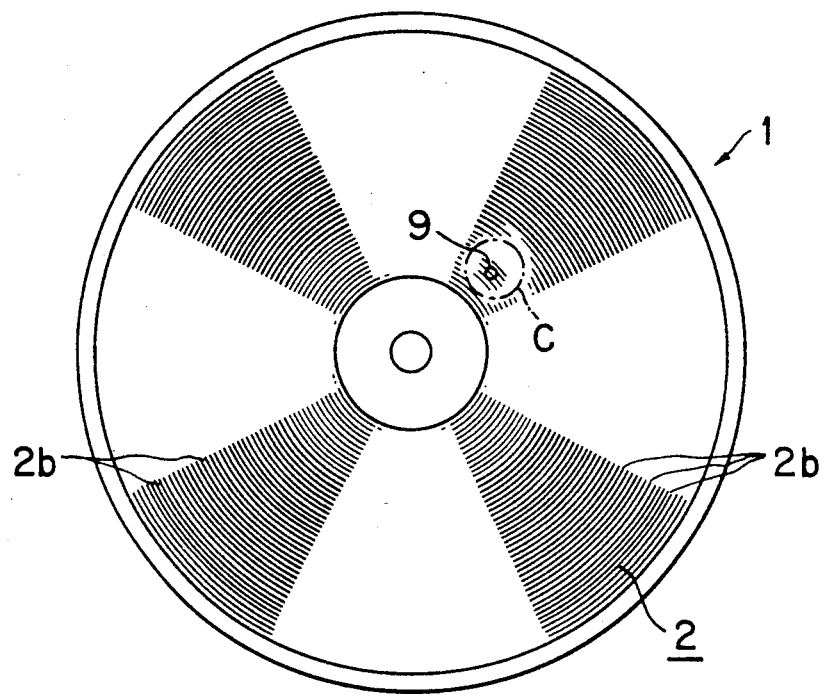
FIGS. 10A and 10B are plan views respectively showing the entire appearance and the expanded data recording track of an optical disk as an object of detection according to the second embodiment shown in FIG. 9.
Figure 10B:
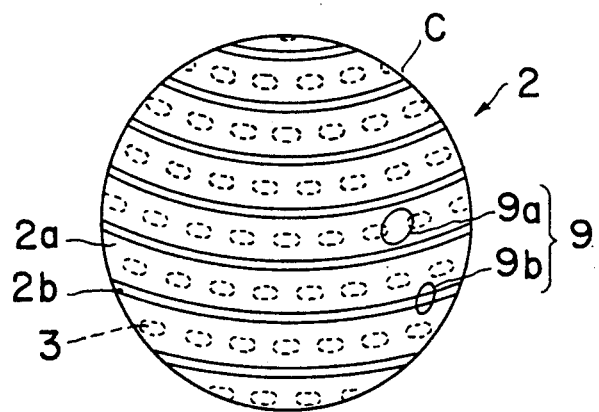

The second embodiment of the defect detection system of this invention is described in detail according to FIGS. 9, 10A and 10B.

The detection system according to the second embodiment is different from that of the first embodiment at the point of changing the optical recording medium as the object of detection from the optical card to an optical disk 1.

In FIG. 9, the data recording portion 2 of the optical disk 1 is formed with a radius of 60 mm. Accordingly, the whole defective portions of the portion 2 can be detected by detection of the linear sensor 25 with 60 mm wide and by a rotation of the disk 1 by a rotating device 17. The disk 1 is set on an upper surface of a turntable 18 provided in the rotating device 17. The turntable 18 has a plurality of suction holes 16 which are open on a disk setting surface and absorb the disk 1 by vacuum force the same as in the first embodiment. The configuration without the above description is substantially the same as the first embodiment.

The operation in the second embodiment is substantially the same as the first embodiment without detecting the defective portions in the portion 2 while a rotation of the disk 1 as the object of detection, so that explanation will be omitted. However, the equations (2) to (5) according to a principle of the operation change to the following equations (6) to (9) on the basis of a specific size of the disk 1. Though the CCD linear sensor 25 has the same number of pixels and the same width as the first embodiment, the system according to the second embodiment detects the portion 2 having 60 mm in width by divided into three times, that is, by three rotations of the disk 1. The optical disk 1 has a groove being 0.8 μm in width and having pitch of 2 μm and the size of the defective portion to be detected is substantially 10 μm by reason of a reproducing reader.

$$W_G \leq W_C/n \leq W_D \tag{1}$$

from the above-mentioned conditions, $$\left. \begin{array}{l} W_G = 0.8 \ (\mu m) \\ W_C = 10 \ (\mu m) \\ W_D = 10 \ (\mu m) \end{array} \right\} \tag{6}$$

The magnifying power n is obtained by substituting equations (6) into (1), $$1 \leq n \leq 12.5 \tag{7}$$

where the magnifying power n is set to one and half times, and the linear sensor scans the recording portion 2 having 60 mm in width by three times, $$W_V = 4,096 \times 10/1.5 \times 3 = 81,920 \ (\mu m) \tag{8}$$

$$W_R = 60 \times 1000 = 60,000 \ \mu m) \tag{9}$$

As described above, int he case where the optical recording medium is applied by the optical disk 1, the condition of "$W_V > W_R$" is satisfied, and it is possible to put the width of the recording portion 2 within the field of view.

Though both the first and second embodiments use the linear sensor 25 as the reflected ray detection means, it is a matter of course that the present invention is capable of utilizing by configuration of the detection means which uses the two-dimensional image sensor. In this case, the image window processing circuit 33 can be omitted from the processor 30 because the circuit 33 processes the image signals corresponding to a line. However, the image sensor is rather expensive with comparison to the linear sensor.

Though the reflected ray control means 24 has a configuration of the lengthened diaphragm 24a and the imaging lens 24b, this invention is not limited to this configuration and may have the control means 24 by transmission type or reflection type diffraction grating lens to transmit only the specific rays.

What is claimed is:

1. A system for detecting defective portions in a data recording portion of an optical recording medium, comprising:
    light radiation means for irradiating a light beam on a data recording portion of said optical recording medium as an object of detection, said data recording portion comprising at least a tracking groove for making a recording track;
    object position regulating means for regulating a position of said data recording portion in a manner that said light beam is irradiated to desired portions of said data recording portion;
    lens means for receiving reflected light from a surface of said data recording portion, said lens means having a magnifying power which resolves said defective portions only without resolving said tracking groove; and detection means for detecting said reflected light from said defective portions without detecting said tracking groove in said data recording portion.

2. The system of claim 1, wherein:

said optical recording medium is an optical card; and said regulating means comprises a card position regulating mechanism which carries said optical card on an upper surface thereof and which moves in two directions arranged perpendicularly on a two-dimensional plane in order to irradiate said light beam to a desired portion of said optical card.

3. The system of claim 2, wherein said card position regulating mechanism has a stage for carrying said card on an upper surface thereof and has a plurality of suction holes on said upper surface for holding said card on said stage.

4. The system of claim 1, wherein:

said optical recording medium is an optical disk; and said regulating means comprises a disk position regulating mechanism which carries said optical disk on an upper surface thereof and which rotates on a two-dimensional plane in order to irradiate said light beam to a desired portion of said optical disk.

5. The system of claim 4, wherein said disk position regulating mechanism has a stage for carrying said disk on an upper surface thereof and has a plurality of suction holes on said upper surface for holding said disk on said stage.

6. The system of claim 1, wherein:

said light radiation means comprises a point light source comprising a condenser lens in order to condense said light beam to said data recording portion at an optical axis of an optical system; and said lens means comprises an imaging lens for imaging only said reflected light from said defective potions onto said detection means, and a diaphragm for limiting a light beam at an optical axis of said imaging lens.

7. The system of claim 6, wherein:

said diaphragm of said lens means has a slit-shaped opening such that reflected light is imaged onto said detection means in a straight shape; and said detection means further comprises a linear sensor which detects said light of said straight shape in one-dimension.

8. The system of claim 6, wherein:

said diaphragm of said lens means has a predetermined extent to which it is open such that reflected light is imaged onto said detection means with a predetermined area in two-dimensions.

9. The system of claim 1, wherein:

said light radiation means comprises a high-frequency wave fluorescent lamp which is powered by a high-frequency wave power source and which irradiates a wide, uniform light beam;

said lens means comprises an imaging lens for imaging only reflected light from said defective portions onto said detection means, and a diaphragm for limiting the light at an optical axis of said imaging lens; and said detection means comprises a linear sensor for one-dimensionally detecting a substantially straight line shaped and reflected light beam formed by a uniform light beam reflected from said surface of said data recording portion.

10. The system of claim 1, wherein:

said detection means converts optical data received from said data recording portion into electrical signals via a photoelectric conversion function; and said system further comprises signal processing means which outputs positions, sizes, and characters of defective portions existing in said data recording portion, said output being determined by processing said electrical signals.

11. The system of claim 10, wherein said signal processing means comprises:

a differentiating circuit for receiving said electrical signals which are detected by said detection means and into which are converted by said detection means to video signals and for outputting differentiated video signals after differentiation processing;

a binary circuit for converting said differentiated video signal into digitized signals and for outputting digitized video data;

a defect detecting portion for detecting defect data corresponding to said defective portions based on said video data; and a judgment circuit for outputting video valid/invalid judgment signals for recognizing a start and end of defect detection operation based on said judgment signals.

12. The system of claim 11, wherein said signal processing means further comprises:

an image window processing circuit provided between said binary circuit and said defect detecting portion for processing necessary image data out of said video data output from said binary circuit in order to detect said defective portions and for ignoring data without said necessary image data.

13. The system of claim 12 wherein said signal processing means further comprises:

a defect data memory for storing said defect data output from said defect detecting portion; and an image data memory for storing said image data output from said image window processing circuit.

14. The system of claim 11, wherein said system further comprises;

a central processing unit for processing said defect in accordance with scratches and dust existing in said recording portion corresponding to positions, sizes and characters of said defective portions based on said defect data output from said defect detecting portion and said judgment signals output form said judgment circuit.

15. The system of claim 14, wherein said central processing unit is connected to and controls said light irradiation means, object position regulating means, lens control means, and detection means.

16. The system of claim 14, wherein said central processing unit is connected to a display unit for displaying said defect data and a printer capable of visually and numerically printing said defect data.

* * * * *